(12) United States Patent
Chou

(10) Patent No.: US 8,201,278 B2
(45) Date of Patent: Jun. 19, 2012

(54) SWIMMING GOGGLES

(76) Inventor: Terry Chou, Tainan (TW)

( * ) Notice: Subject to any disclaimer, the term of this patent is extended or adjusted under 35 U.S.C. 154(b) by 318 days.

(21) Appl. No.: 12/768,499

(22) Filed: Apr. 27, 2010

(65) Prior Publication Data

US 2011/0258761 A1 Oct. 27, 2011

(51) Int. Cl.
*A61F 9/02* (2006.01)
(52) U.S. Cl. .................................. 2/426; 2/441; 2/443
(58) Field of Classification Search .............. 2/448, 449, 2/450, 452, 453, 426, 440, 442, 445, 441, 2/443; 351/43
See application file for complete search history.

(56) References Cited

U.S. PATENT DOCUMENTS

| | | | | |
|---|---|---|---|---|
| 2,680,846 A * | 6/1954 | Hirschmann | | 2/441 |
| 2,773,260 A * | 12/1956 | Hirschmann | | 2/441 |
| 5,896,588 A * | 4/1999 | Chiang | | 2/428 |
| 5,896,589 A * | 4/1999 | Chou | | 2/428 |
| 6,948,813 B2 * | 9/2005 | Parks | | 351/158 |
| 7,003,811 B2 * | 2/2006 | Canavan | | 2/448 |
| 7,162,750 B2 * | 1/2007 | Canavan | | 2/448 |
| 7,322,051 B1 * | 1/2008 | Wang | | 2/448 |
| 7,490,365 B2 * | 2/2009 | Matsumoto et al. | | 2/448 |
| 7,604,346 B2 * | 10/2009 | Wang | | 351/43 |
| 7,698,751 B2 * | 4/2010 | Chiang | | 2/450 |
| 7,882,575 B2 * | 2/2011 | Wang-Lee | | 2/431 |
| 2008/0134417 A1 * | 6/2008 | Aoyama | | 2/431 |

* cited by examiner

*Primary Examiner* — Alissa L Hoey
*Assistant Examiner* — Amber Anderson

(57) ABSTRACT

A pair of swimming goggles includes two rigid lenses each having an extension. A stub is formed on a front side of each extension, and a button is formed on a distal end of the stub. A frame includes two ring portions receiving the lenses. Each ring portion includes a receptacle extending into an outer side of the ring portion. The outer side of each ring portion includes front and rear walls delimiting the receptacle, and a through-hole extends through the front wall. The extensions of the lens are received in the receptacles. The stub of each lens extends through the through-hole of the outer side of one of the ring portions. The button of each lens is located outside of the frame. A coupling plate is mounted to each lens and has a through-hole through which the stub of one of the lenses extends.

6 Claims, 11 Drawing Sheets

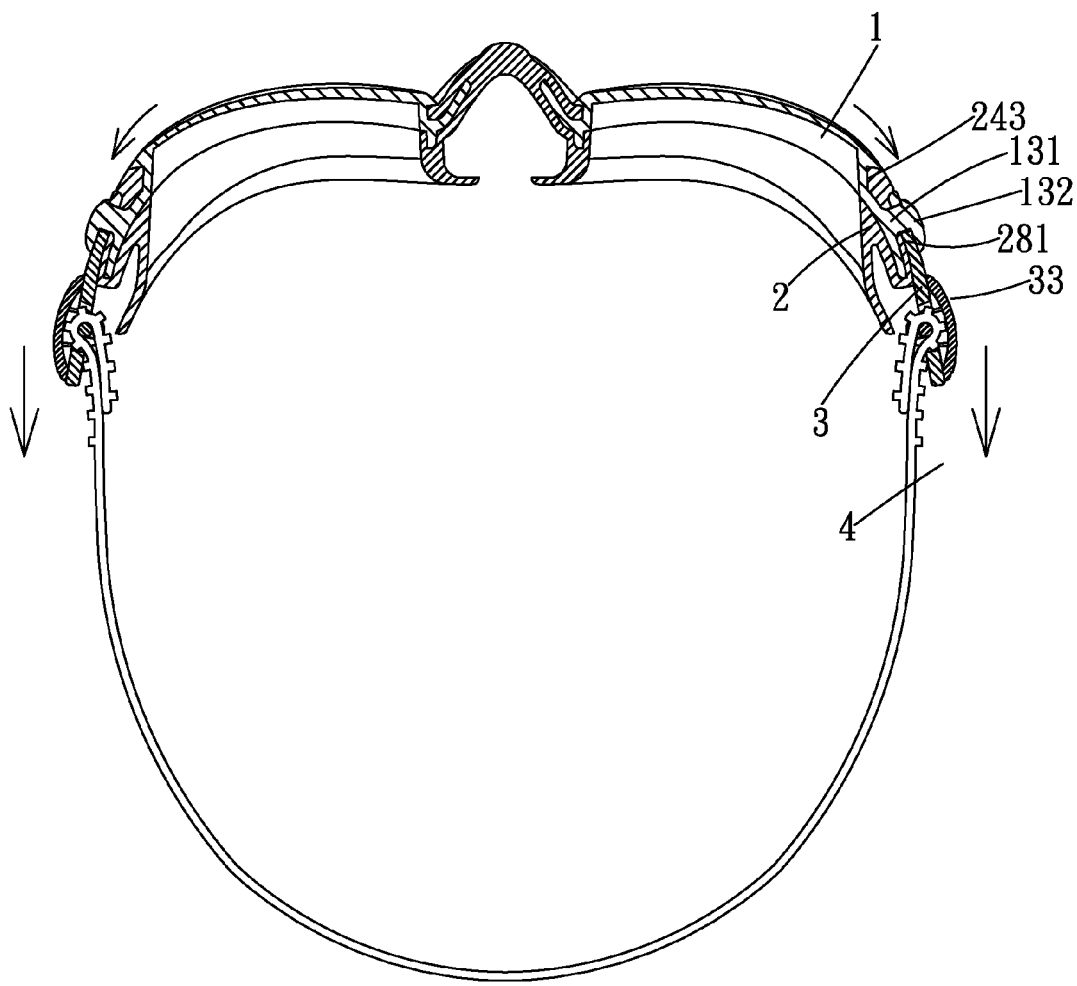
F I G . 6

SWIMMING GOGGLES

BACKGROUND OF THE INVENTION

1. Field of the Invention

The present invention relates to a pair of swimming goggles and, more particularly, to a pair of swimming goggles that is enhanced in assembling stability, combination variety, application, and quality impression.

2. The Description of the Related Art

FIG. 9 shows a pair of conventional swimming goggles including two rigid lenses 1', two soft padding members 2', a bridge 1', and a head strap 4'. Each lens 1' includes a flange 11' formed on a rear end thereof, a bridge engaging portion 12' formed on an inner side thereof, and a head strap engaging portion 13' on an outer side thereof. Each padding member 2' includes an annular groove 21' in a front portion thereof for receiving the flange 11' of one of the lenses 1'. Each padding member 2' further includes a padding portion 22' on a rear portion thereof. A bridge 3' is engaged with the bridge engaging portions 12' of the lenses 1'. A head strap 13' includes two ends respectively engaged with the head strap engaging portions 13' of the lenses 1'. However, the lenses 1' are liable to disengage from the annular grooves 21' of the padding members 2' when the padding members 2' are impinged by external force. Furthermore, the head strap engaging portion 13' can only be coupled with a head strap 4' of a corresponding type.

FIG. 10 shows another pair of conventional swimming goggles including a frame 6' made of soft material. The frame 6' includes a padding portion 61', two head strap engaging portions 62' for engaging two ends of a head strap 7', a bridge portion 63', and two annular grooves 64' receiving two lenses 5'. However, when the head strap 7' is pulled while wearing the pair of swimming goggles, the annular grooves 64' of the frame 6' are liable to expand at outer portions thereof, leading to leakage of water or disengagement of the lenses 5'. Furthermore, the head strap engaging portion 62' can only be coupled with a head strap 7' of a corresponding type.

Thus, a need exists for pair of swimming goggles that is enhanced in assembling stability, combination variety, application, and quality impression.

BRIEF SUMMARY OF THE INVENTION

The present invention solves this need and other problems in the field of reliable assembly and large applications of swimming goggles by providing, in a preferred form, a pair of swimming goggles includes two lenses made of transparent, rigid material and each having a flange formed on a rear end thereof. Each lens further includes an extension on an outer side thereof. The extension of each lens has a front face. A stub is formed on the front side of the extension of each lens. A button is formed on a distal end of the stub of the extension of each lens with a spacing defined between a bottom face of the button and the front face of the extension. A frame is made of soft material and includes a bridge on a central portion thereof and a padding portion on a rear side thereof. The frame further includes two ring portions each having an annular groove receiving the flange of one of the lenses. Each ring portion further includes a receptacle extending into an outer side of the ring portion. The outer side of each ring portion includes front and rear walls delimiting the receptacle. A through-hole extends through the front wall of the outer side of each ring portion. The extension of each lens is received in the receptacle of one of the ring portions. The stub of each lens extends through the through-hole of the outer side of one of the ring portions. The button of each lens is located outside of the frame. Two coupling plates are made of rigid material and each include a lens coupling portion coupled with one of the two lenses and a head strap coupling portion engaged with a head strap. The lens coupling portion includes a through-hole through which the stub of one of the lenses extends.

In preferred forms, the front wall of the outer side of each ring portion and the lens coupling portion of one of the coupling plates are securely received in the spacing between the bottom face of the button and the front face of the extension of one of the two lenses. The outer side of each ring portion includes a front surface having a recessed section. The through-hole extends through the front wall to the recessed section. The lens coupling portion of each coupling plate is received in the recessed section of one of the ring portions. The lens coupling portion of each coupling plate includes a slit extending from the through-hole to provide the through-hole with expanding flexibility. The front wall of the outer side of each ring portion includes an abutting edge abutting a side of one of the lenses.

In a preferred form, a spacing between a front end of the button of each lens and a periphery of the stub of the lens is smaller than a spacing between a rear end of the button of the lens and the periphery of the stub of the lens.

When the head strap is pulled, the force applied to the head strap is imparted to the coupling plates and the stubs of the rigid lenses instead of directly stretching the soft frame, reducing deformation of the frame. Since the stubs extend through the through-holes of the frame and since each lens has a side abutting one of the abutting edges of the frame, the force applying direction will cause the lens to firmly abut the abutting edge when the lens is subjected to force. Thus, the outer sides of the frame and the lenses have enhanced assembling stability and enhanced waterproof effect.

The present invention will become clearer in light of the following detailed description of illustrative embodiments of this invention described in connection with the drawings.

DESCRIPTION OF THE DRAWINGS

The illustrative embodiments may best be described by reference to the accompanying drawings where:

FIG. 5A shows an enlarged view of a circled portion of FIG. 5.

FIG. 6 shows a top, cross sectional view of the pair of swimming goggles of FIG. 1.

Figure 1:
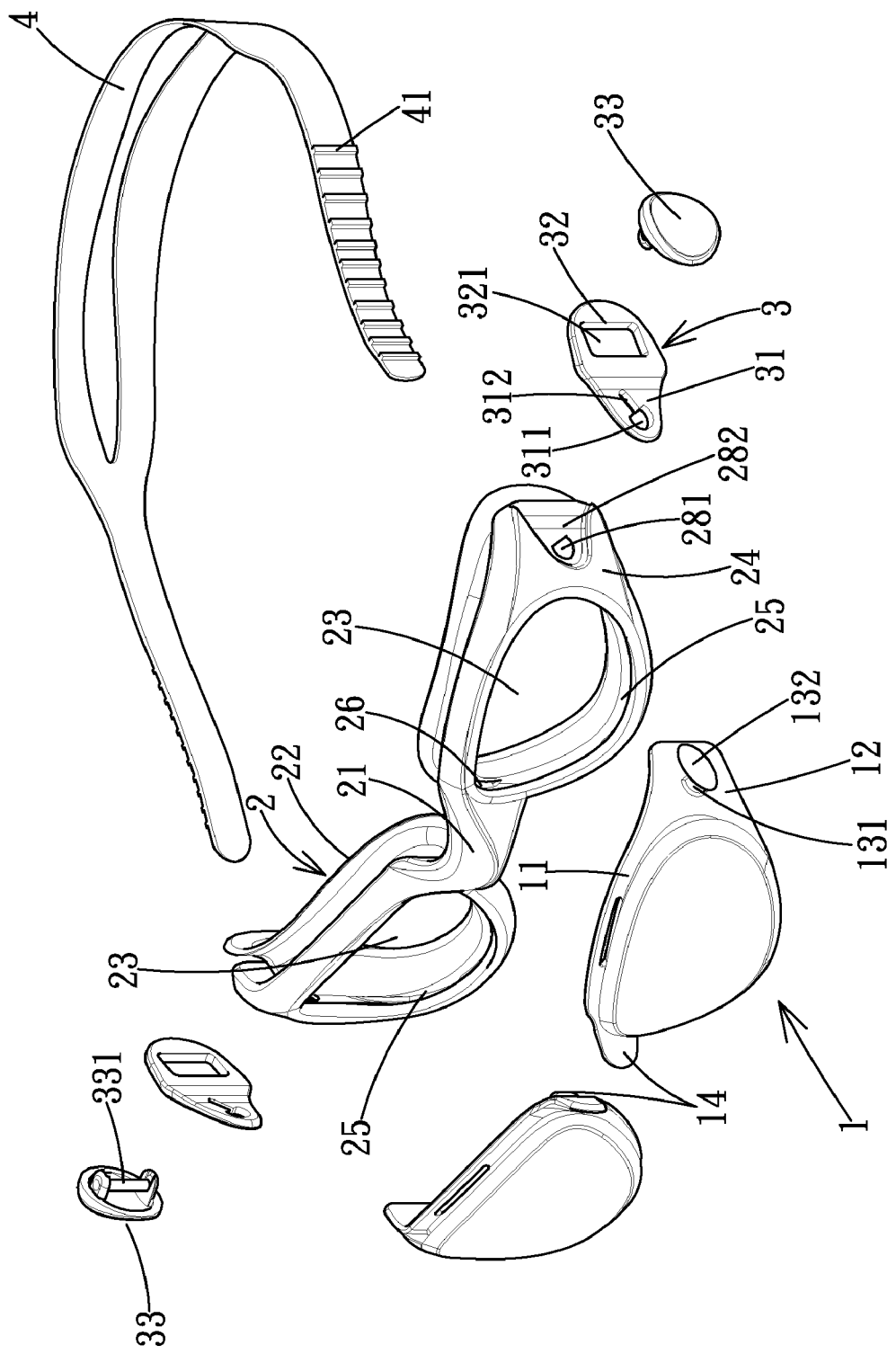
FIG. 1 shows an exploded, perspective view of a pair of swimming goggles of a first embodiment according to the preferred teachings of the present invention.
Figure 2:
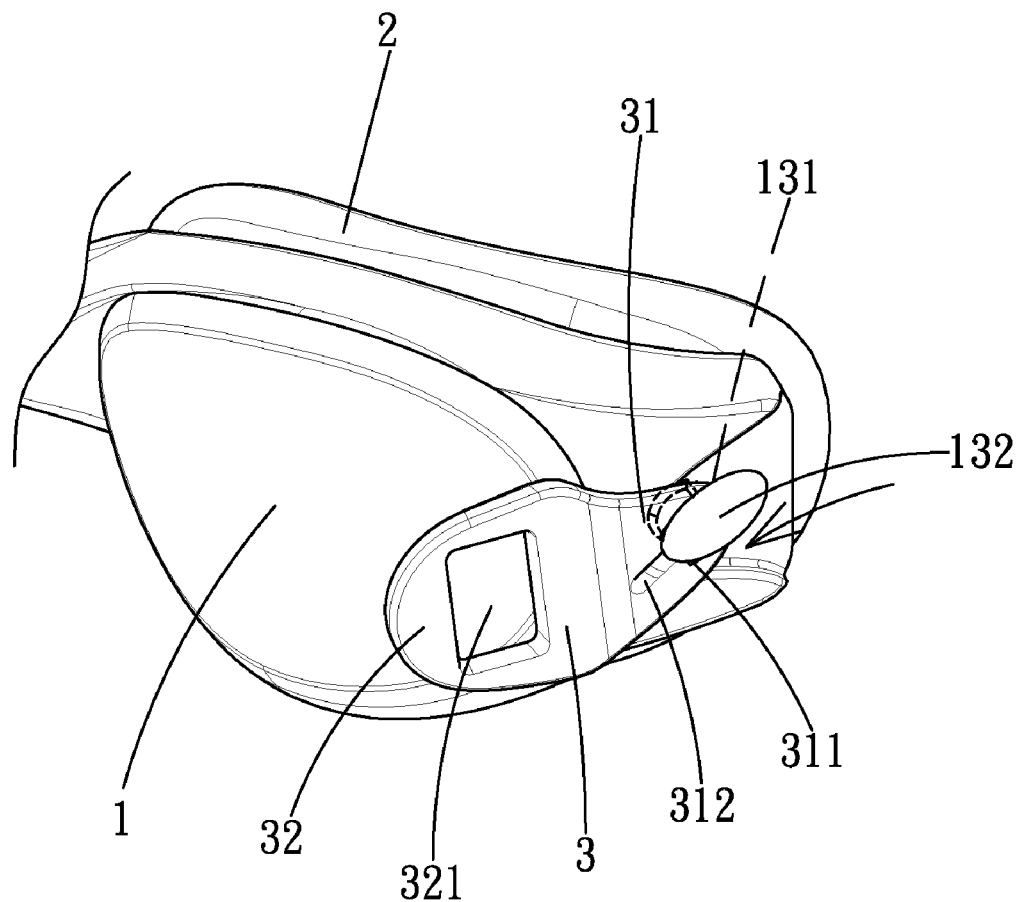
FIG. 2 shows a partial, perspective view of the pair of swimming goggles of FIG. 1 with a coupling plate mounted to a lens.
Figure 3:
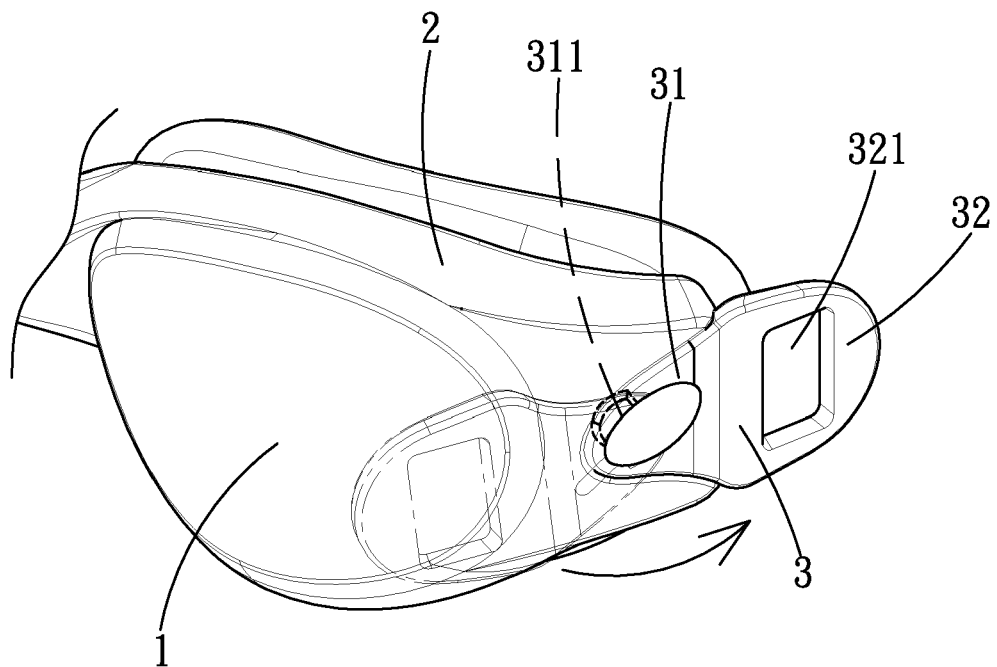
FIG. 3 shows a partial, perspective view of the pair of swimming goggles of FIG. 1 with the coupling plate pivoted to a position ready for coupling with an end of a head strap.
Figure 4:
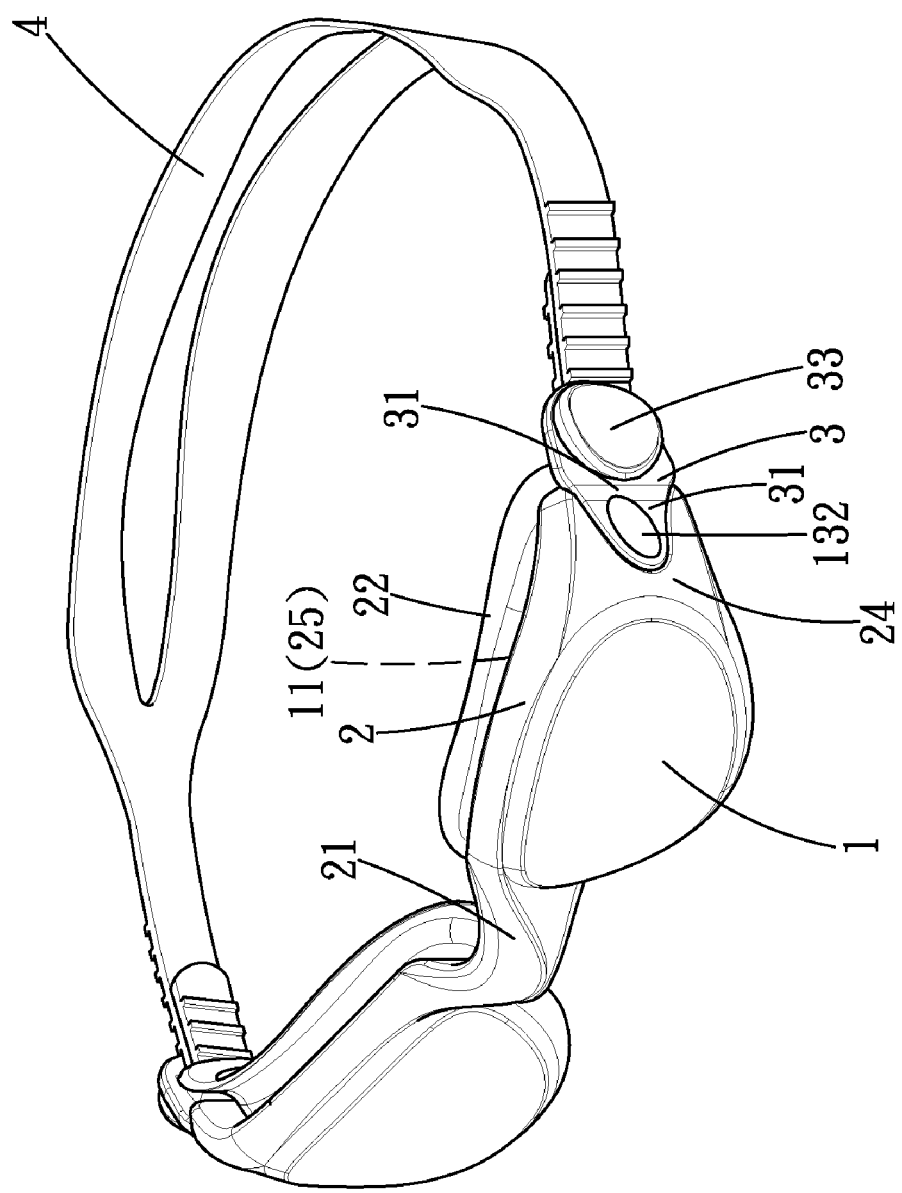
FIG. 4 shows a perspective view of the pair of swimming goggles of FIG. 1 after assembly.

All figures are drawn for ease of explanation of the basic teachings of the present invention only; the extensions of the figures with respect to number, position, relationship, and dimensions of the parts to form the preferred embodiments will be explained or will be within the skill of the art after the following teachings of the present invention have been read and understood. Further, the exact dimensions and dimensional proportions to conform to specific force, weight, strength, and similar requirements will likewise be within the skill of the art after the following teachings of the present invention have been read and understood.

DETAILED DESCRIPTION OF THE INVENTION

With reference to FIGS. 1-6, a pair of swimming goggles of a first embodiment according to the preferred teachings of the present invention generally includes two lenses 1, a frame 2, two coupling plates 3, and a head strap 4. Each lens 1 is made of transparent, rigid material and includes a flange 11 on a rear end thereof. Each lens 1 further includes an extension 12 on an outer side thereof adjacent a temple of a wearer wearing the pair of swimming goggles. A stub 131 is formed on a front face of the extension 12 of each lens 1, and a button 132 is formed on a distal end of the stub 131 with a spacing C (FIG. 5A) defined between a bottom face of the button 132 and the front face of the extension 12. Each button 132 is substantially elliptical when viewed from a top side thereof. Each button 132 includes front and rear ends. A spacing A between the front end of the button 132 and a periphery of the stub 131 is smaller than a spacing B between the rear end of the button 132 and the periphery of the stub 131 (FIG. 5A). Each lens 1 further includes an insert 14 formed on an inner side thereof adjacent a nose of the wearer wearing the pair of swimming goggles.

The frame 2 is made of soft material and includes a bridge 21 on a central portion thereof. The frame 2 further includes two ring portions 23 receiving the lenses 1. Specifically, each ring portion 23 includes an annular groove 25 receiving the flange 11 of one of the lenses 1. Each ring portion 23 further includes an insert groove 26 receiving the insert 14 of one of the lenses 1. In the preferred forms shown in FIGS. 1-8, the insert groove 26 includes two groove sections receiving the insert 14 in the form of two fingers. A padding portion 22 is formed on a rear side of the frame 2. In the preferred forms shown in FIGS. 1-8, a padding portion 22 is formed on a rear side of each ring portion 23. An outer side 24 of each ring portion 23 includes a front surface having a recessed section 282. Each ring portion 23 further includes a receptacle 27 extending into the outer side 24 thereof. The outer side 24 includes front and rear walls 241 and 242 delimiting the receptacle 27. An outer edge of the front wall 241 is integrally formed with an outer edge of the rear wall 242 as a single continuous monolithic piece. The front wall 241 includes an abutting edge 243 adjacent the ring portion 23. A through-hole 281 extends through the front wall 241 to the recessed section 282 and is in communication with the receptacle 27.

Each coupling plate 3 is made of rigid material and includes a lens coupling portion 31 for engaging with one of the lenses 1 and a head strap coupling portion 32 for engaging with one of two ends of the head strap 4. The lens coupling portion 31 of each coupling plate 3 is configured to correspond to the shape of one of the recessed portions 282 of the frame 2 and includes a through-hole 311 through which the stub 131 of one of the lenses 1 extends. A slit 312 extends from the through-hole 311 to provide the through-hole 311 with expanding flexibility. The head strap coupling portion 32 of each coupling plate 3 includes n opening 321 for engaging with one of two ends of the head strap 4. The head strap 4 includes a plurality of positioning ridges 41. A cap 33 can be mounted to each coupling plate 3 to cover the opening 321, providing an aesthetic appearance. Each cap 33 includes a peg 331 around which an end of the head strap 4 extends.

Figure 5:
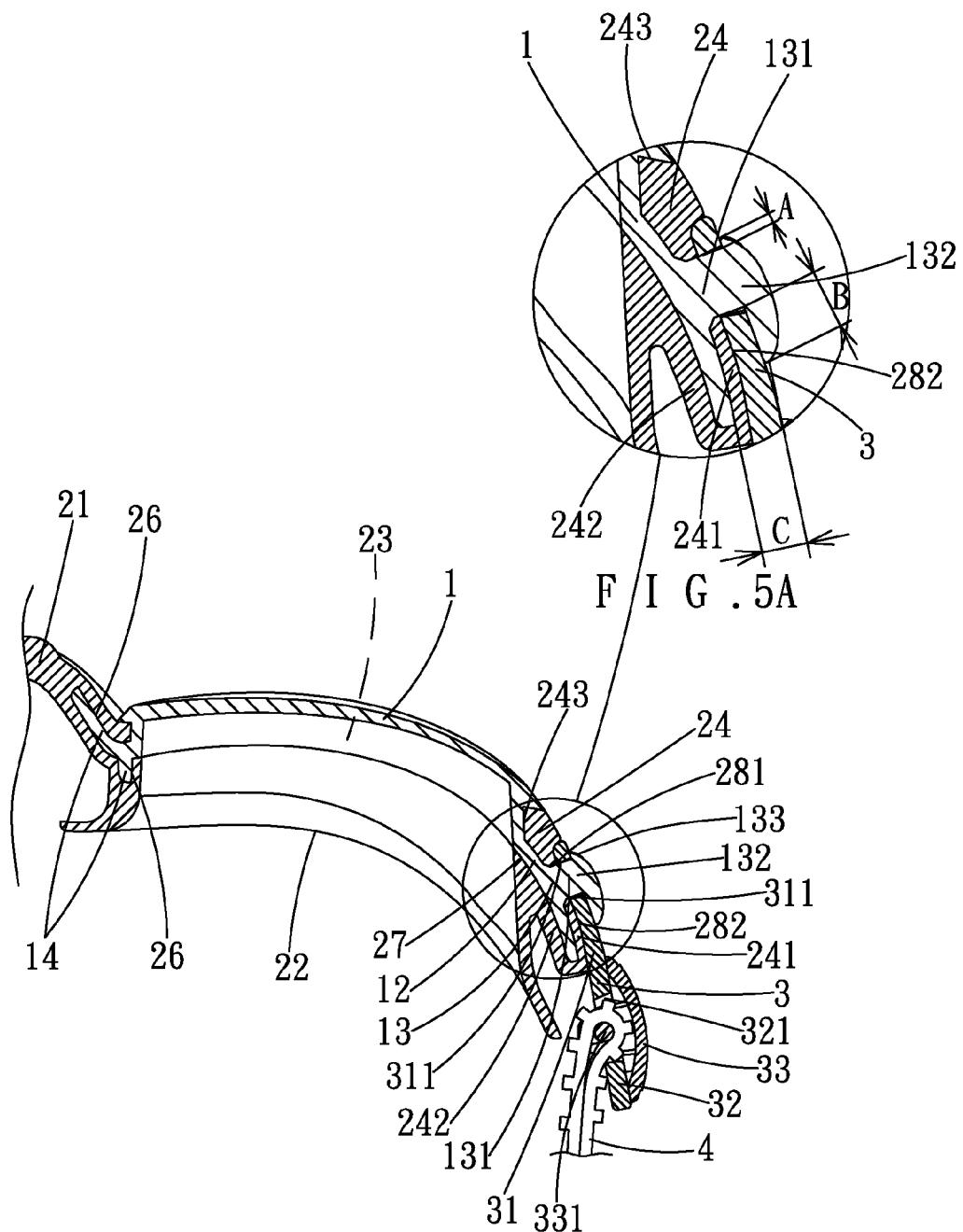
FIG. 5 shows a partial, cross sectional view of the pair of swimming goggles of FIG. 1.
Figure 7:
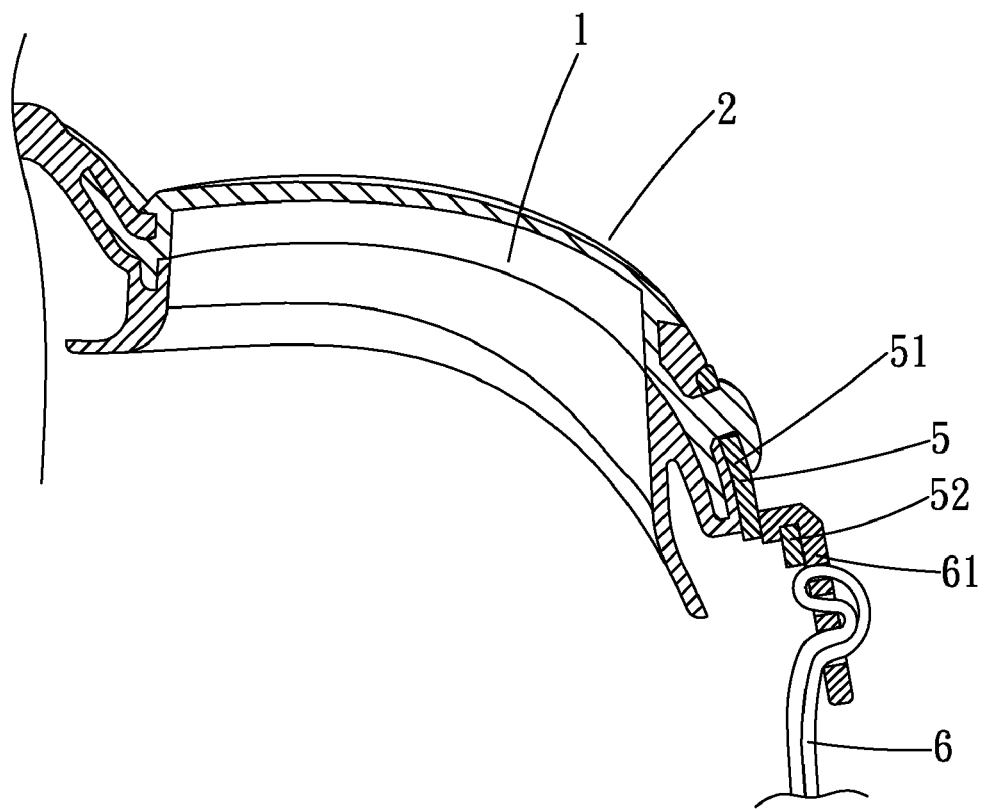
FIG. 7 shows a partial, cross sectional view of a pair of swimming goggles of a second embodiment according to the preferred teachings of the present invention.
Figure 8:
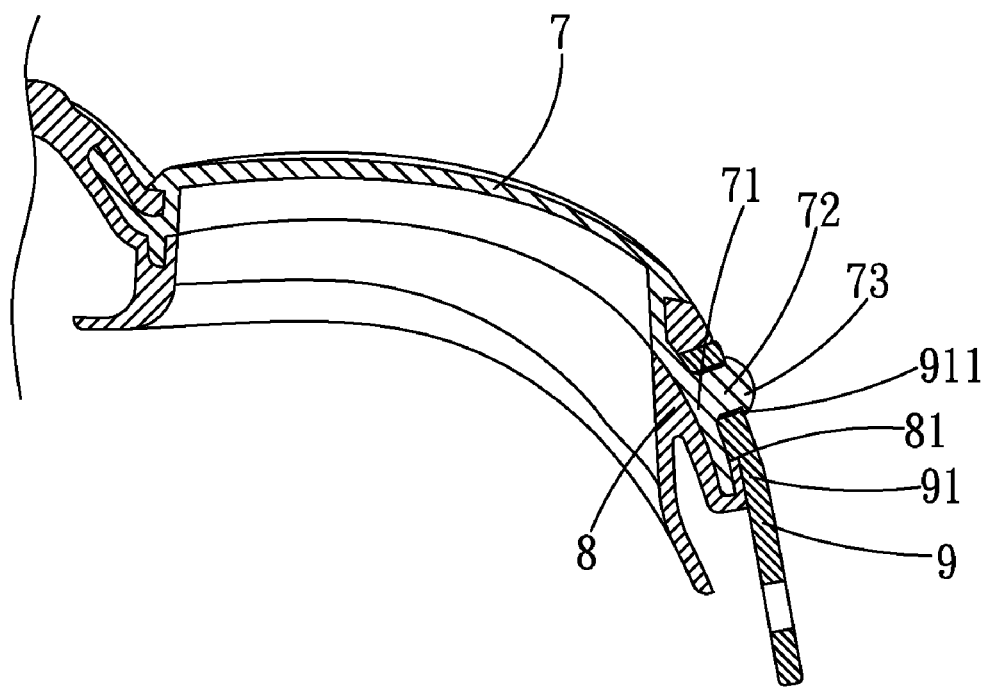
FIG. 8 shows a partial, cross sectional view of a pair of swimming goggles of a third embodiment according to the preferred teachings of the present invention.
Figure 9:
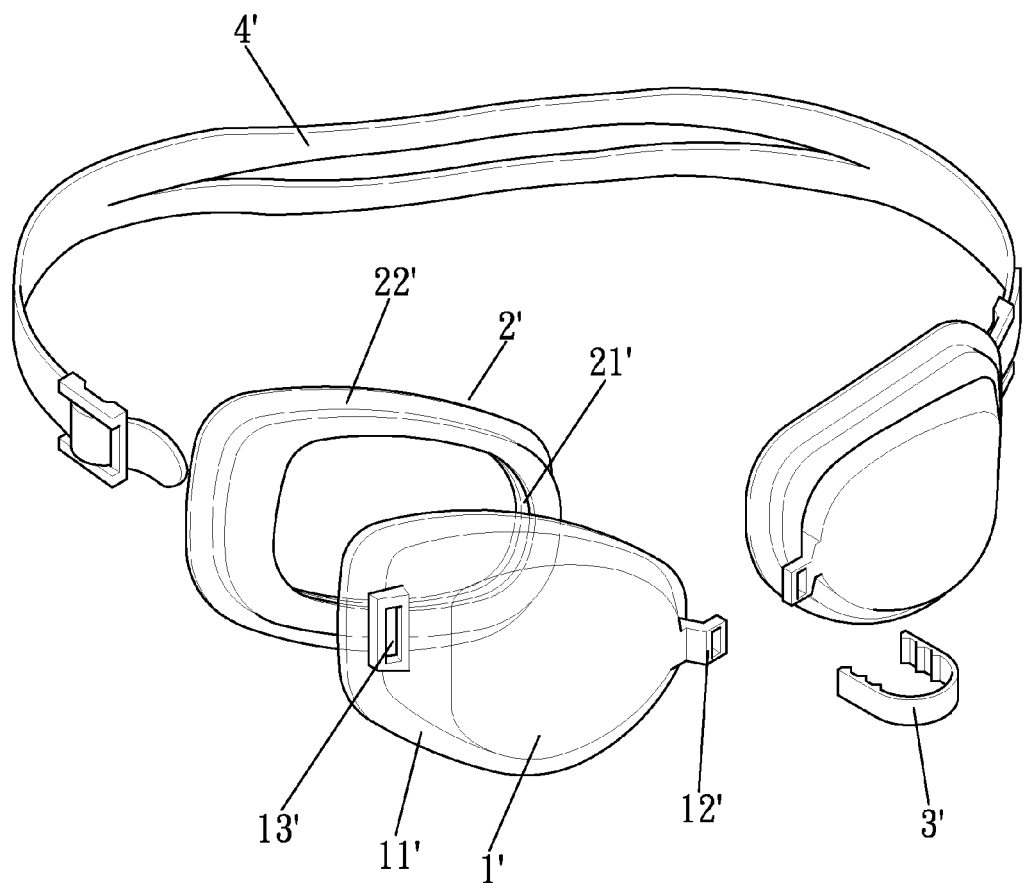
FIG. 9 shows an exploded, perspective view of a pair of conventional swimming goggles.
Figure 10:
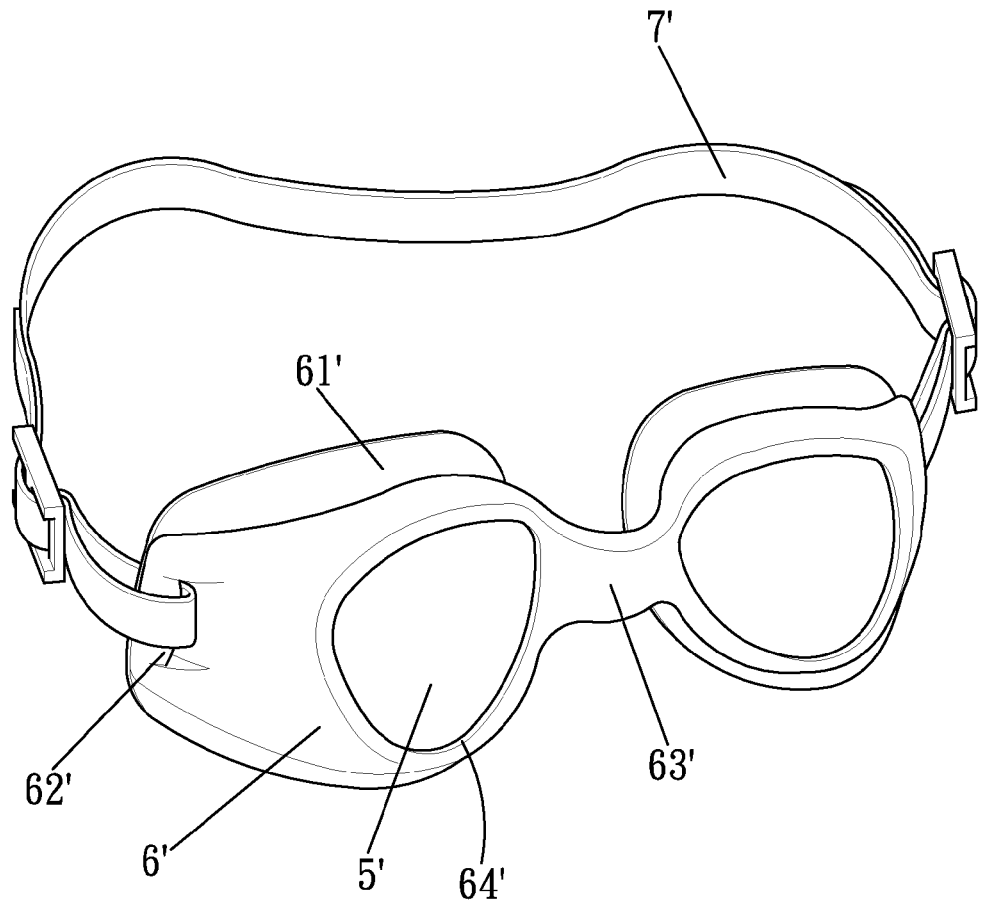
FIG. 10 shows a perspective view of another pair of conventional swimming goggles.
Figure 11:
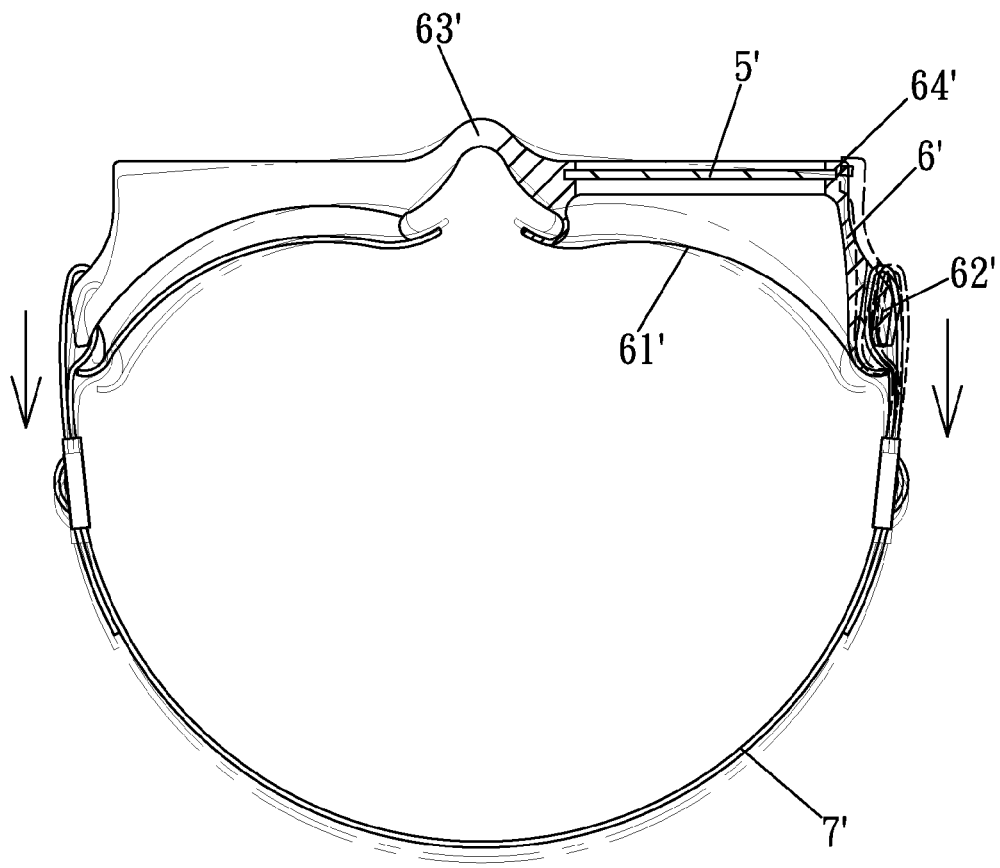
FIG. 11 shows a top view of the pair of conventional swimming goggles of FIG. 10 with a portion of the pair of swimming goggles cross sectioned.

In assembly, the extension 12 of each lens 1 is extended into one of the receptacles 27 of the soft frame 2 by the resiliency of the soft frame 2 with the extension 12 located in the outer side 24 of the frame 2 and sandwiched between the front and rear walls 241 and 242, with the stub 132 and the button 131 of the lens 1 extending through the through-hole 281 of the frame 2 to the recessed section 282, and with the abutting edge 243 of the frame 2 abutting a side of the lens 1. Furthermore, the flange 11 of each lens 1 is received in one of the annular grooves 25 of the frame 2 (FIG. 4) with the insertion 14 of the lens 1 received in one of the insert grooves 26 of frame 2. Thus, disengagement of the extensions 12 of the lenses 1 from the outer sides 24 of the frame 2 is avoided, assuring reliable engagement between the lenses 1 and the frame 2 and providing enhanced waterproof effect. Note that the stub 132 of each lens 1 is located outside of the frame 2. Furthermore, the head strap coupling portion 32 of each coupling plate 3 firstly faces the center of the lens 1 (FIG. 2), and the through-hole 311 is engaged with a longer side of one of the buttons 132. After engagement, the coupling plate 3 is pivoted rearward to a position shown in FIG. 3 with the slit 312 providing the through-hole 311 with expanding flexibility. Thus, the through-hole 311 receives the stub 131 of one of the lenses 1. Furthermore, the lens coupling portion 31 of each coupling plate 3 is received in one of the recessed sections 282 of the frame 2 with the front wall 241 and the lens coupling portion 31 securely received in the spacing C between the front face of the extension 12 and the bottom face of the button 132 of the lens 1, as shown in FIGS. 5 and 5A. The soft front wall 241 provides a tightening function as well as tight assembly.

The recessed sections 282 of the frame 2 receive the lens coupling portions 31 of the coupling plates 3, avoiding protrusion of the coupling plates 3 out of the outer sides 24 of the frame 2, enhancing quality impression. The caps 33 mounted to the head strap coupling portions 32 also enhance the quality impression. It is noted that the positioning ridges 41 on the head strap 4 are engaged with edges of the openings 32 of the head strap coupling portions 32 to provide the desired positioning effect.

With reference to FIG. 6, when a user pulls the head strap 4 while wearing the pair of swimming goggles or for other reasons, the force applied to the head strap 4 is imparted to the coupling plates 3 and the stubs 131 of the rigid lenses 1 instead of directly stretching the soft frame 2, reducing deformation of the frame 2. Since the stubs 131 extend through the through-holes 281 of the frame 2 and since each lens 1 has a side abutting one of the abutting edges 243 of the frame 2, the force applying direction will cause the lens 1 to firmly abut the abutting edge 243 when the lens 1 is subjected to force. Thus, the outer sides 24 of the frame 2 and the lenses 1 have enhanced assembling stability and enhanced waterproof effect.

The swimming goggles according to the preferred teachings of the present invention can be utilized with differing head straps by simply changing the coupling plates 3. In a second embodiment shown in FIG. 7, the coupling plates 3 are replaced with two coupling plates 5 each having a lens coupling portion 51 identical to the lens coupling portion 31 and a head strap coupling portion 52 of another type, such that the head strap coupling portion 52 can be engaged with a head strap 6 of the type having a buckle 61 on each of two ends of the head strap 6. Thus, the swimming goggles according to the preferred teachings of the present invention can be utilized with head straps corresponding to the types of the coupling plates 5 without changing the lenses 1 and the frame 2.

The buttons 132 can be of other shapes and sizes. In a third embodiment shown in FIG. 8, the button (now designated 73) on the distal end of the stub (now designated 72) of the extension (now designated 71) of each lens (now designate 7) is spherical when viewed from a top side. Each through-hole (now designated 81) of the frame (now designated 8) has a larger diameter. The lens coupling portion (now designated 91) of each coupling plate (now designated 9) has a thickness corresponding to the spacing between the front face of the extension 71 and the bottom face of the button 73. The lens coupling portion 91 has a through-hole 911 through which the stub 72 extends by force fitting. Thus, the lens coupling portion 91 is sandwiched between the button 73 and the extension 71 to avoid disengagement, although the lens coupling portion 91 is not tightened as the lens coupling portion 31 tightened by the front wall 241 in the first embodiment.

Thus since the invention disclosed herein may be embodied in other specific forms without departing from the spirit or general characteristics thereof, some of which forms have been indicated, the embodiments described herein are to be considered in all respects illustrative and not restrictive. The scope of the invention is to be indicated by the appended claims, rather than by the foregoing description, and all changes which come within the meaning and range of equivalency of the claims are intended to be embraced therein.

The invention claimed is:

1. A pair of swimming goggles comprising:
   two lenses made of transparent, rigid material and each including a flange formed on a rear end thereof, with each of the two lenses further including an extension on an outer side thereof, with the extension of each of the two lenses having a front face, with a stub being formed on the front side of the extension of each of the two lenses, with a button formed on a distal end of the stub of the extension of each of the lenses with a spacing defined between a bottom face of the button and the front face of the extension;
   a frame made of soft material and including a bridge on a central portion thereof and a padding portion on a rear side thereof, with the frame further including two ring portions each having an annular groove receiving the flange of one of the two lenses, with each of the two ring portions further including a receptacle extending into an outer side of the ring portion, with the outer side of each of the two ring portions including front and rear walls delimiting the receptacle, with a through-hole extending through the front wall of the outer side of each of the two ring portions, with the extension of each of the two lenses received in the receptacle of one of the two ring portions, with the stub of each of the two lenses extending through the through-hole of the outer side of one of the two ring portions, with the button of each of the two lenses located outside of the frame;
   two coupling plates made of rigid material and each including a lens coupling portion coupled with one of the two lenses and a head strap coupling portion, with the lens coupling portion including a through-hole through which the stub of one of the two lenses extends; and
   a head strap engaged with the head strap coupling portions of the two coupling plates.

2. The pair of swimming goggles as claimed in claim 1, with the front wall of the outer side of each of the two ring portions and the lens coupling portion of one of the two coupling plates being securely received in the spacing between the bottom face of the button and the front face of the extension of one of the two lenses.

3. The pair of swimming goggles as claimed in claim 1, with the button of each of the two lenses having front and rear ends, with a spacing between the front end of the button of each of the two lenses and a periphery of the stub of the lens being smaller than a spacing between the rear end of the button of the lens and the periphery of the stub of the lens.

4. The pair of swimming goggles as claimed in claim 1, with the outer side of each of the two ring portions including a front surface having a recessed section, with the through-hole extending through the front wall to the recessed section, with the lens coupling portion of each of the coupling plates received in the recessed section of one of the two ring portions.

5. The pair of swimming goggles as claimed in claim 1, with the lens coupling portion of each of the coupling plates including a slit extending from the through-hole to provide the through-hole with expanding flexibility.

6. The pair of swimming goggles as claimed in claim 1, with the front wall of the outer side of each of the two ring portions including an abutting edge abutting a side of one of the two lenses.

\* \* \* \* \*